United States Patent
Sperl et al.

(10) Patent No.: US 11,538,154 B2
(45) Date of Patent: Dec. 27, 2022

(54) METHOD AND DEVICE FOR AUTOMATIC DETERMINATION OF THE CHANGE OF A HOLLOW ORGAN

(71) Applicant: Siemens Healthcare GmbH, Erlangen (DE)

(72) Inventors: Jonathan Sperl, Bamberg (DE); Rainer Kaergel, Forchheim (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 141 days.

(21) Appl. No.: 17/012,281

(22) Filed: Sep. 4, 2020

(65) Prior Publication Data

US 2021/0082110 A1    Mar. 18, 2021

(30) Foreign Application Priority Data

Sep. 12, 2019 (EP) .................................. 19196971

(51) Int. Cl.
  *G06T 7/00*   (2017.01)
  *G06T 7/11*   (2017.01)
  *G06T 7/33*   (2017.01)

(52) U.S. Cl.
  CPC .............. *G06T 7/0012* (2013.01); *G06T 7/11* (2017.01); *G06T 7/337* (2017.01);
  (Continued)

(58) Field of Classification Search
  None
  See application file for complete search history.

(56) References Cited

U.S. PATENT DOCUMENTS 8,805,044 B2    8/2014  Buelow et al.
2007/0116342 A1*   5/2007  Zarkh .................... G06T 7/564
                                                            382/130
(Continued)

FOREIGN PATENT DOCUMENTS

EP      3432215 A1     1/2019
WO   WO-2008138140 A1 * 11/2008  ............. A61B 6/504
WO    WO 2008138140 A1   11/2008

OTHER PUBLICATIONS

Biesdorf, Andreas et al. "Model-Based Segmentation and Motion Analysis of the Thoracic Aorta from 4D ECG-Gated CTA Images" MICCAI2011, International Conference on Financial Cryptography and Data Security, Springer, Berlin, Heidelberg, pp. 589-596, 2011 // ISBN: 978-3-642-17318-9.
(Continued)

*Primary Examiner* — Vu Le
*Assistant Examiner* — Courtney Joan Nelson
(74) *Attorney, Agent, or Firm* — Harness, Dickey & Pierce, P.L.C.

(57) ABSTRACT

A method and device are for automatic determination of the change of a hollow organ. The method includes providing a first medical image of the organ recorded at a first time; computing a first representation of the organ in the first image; computing a first reference-line of the organ based on the first representation and providing a second medical image of the organ recorded at a second point. The method further includes computing a second representation of the organ in the second image; computing a second reference-line of the organ based on the second representation of the organ; registering of the first and second reference-line to obtain at least one of matched representations of the organ and features derived from the matched representations of the organs; and comparing at least one of the matched repre-
(Continued)

sentations of the organs and the features derived from the matched representations of the organ.

20 Claims, 5 Drawing Sheets

(52) U.S. Cl.
CPC ............... *G06T 2207/10081* (2013.01); *G06T 2207/10088* (2013.01); *G06T 2207/30101* (2013.01)

(56) References Cited

U.S. PATENT DOCUMENTS

| | | |
|---|---|---|
| 2010/0309198 A1 | 12/2010 | Kauffmann |
| 2013/0195338 A1* | 8/2013 | Xu .......................... A61B 6/466 382/131 |
| 2019/0019287 A1 | 1/2019 | Reda et al. |
| 2020/0160527 A1 | 5/2020 | Rapaka et al. |

OTHER PUBLICATIONS

Extended European Search Report for European Application No. 19196971.6 dated Jan. 1, 2020.

* cited by examiner

METHOD AND DEVICE FOR AUTOMATIC DETERMINATION OF THE CHANGE OF A HOLLOW ORGAN

PRIORITY STATEMENT

The present application hereby claims priority under 35 U.S.C. § 119 to European patent application number EP19196971.6 filed Sep. 12, 2019, the entire contents of which are hereby incorporated herein by reference.

FIELD

Embodiments of the invention generally relate to a method and a device for automatic determination of the change of a hollow organ on the basis of medical images.

BACKGROUND

Dilations of vessels in the human body are a severe risk for a patient, since these dilations, in particular in the aorta, may progress towards an aneurysm which may burst or cause other adverse effects such as heart attacks, kidney damage or stroke. Thus, early detection of such dilations is critical for many diseases, e.g. for the aorta, i.e. aortic dissection, aortic rupture, and ruptured abdominal aortic aneurysms. Left untreated, such diseases often have severe and potentially fatal consequences. Therefore, it is important to monitor the progression of a dilation of a particular organ.

Additionally, in a post-operative scenario, e.g. after an endovascular aneurysm repair, sac shrinkage is considered to be evidence of clinical success. The problem also can be generalized to any hollow organ such as e.g. other vessels like the airways, or the trachea.

Conventionally, changes of hollow organs are diagnosed by manual evaluation of medical images of a patient, e.g. ultrasound, MR or CT images of an organ under investigation. However, such dilations or shrinkages are often asymptomatic and are only detected after complications have manifested. Thus, it is not possible to diagnose such changes before complications have manifested, resulting in a delayed diagnosis or a failure to diagnose.

SUMMARY

At least one embodiment of the present invention is directed to to improving the known systems, devices and methods to facilitate an improvement in automatic determining the change of hollow organs.

Embodiments are directed to a method, a device, a control device and a medical imaging system.

A method according to at least one embodiment of the invention for automatic determination of the change of a hollow organ, typically on the basis of medical images, and especially also for the visualization of the results, comprises:
  providing a first medical image of the organ, e.g. the aorta, recorded at a first point of time,
  computing a first representation of the organ, e.g. a segmentation mask, in the first image,
  computing a first reference-line of the organ (i.e. a series of points in 3D space characterized by their spatial coordinates, e.g. a centerline) based on the first representation of the organ,
  providing a second medical image of the organ recorded at a second point of time,
  computing a second representation of the organ in the second image,
  computing a second reference-line of the organ based on the second representation of the organ,
  registering of the first and the second reference line to obtain a matching of the two representations of the organ and/or features derived from the representations,
  comparing the matched representations of the organ and/or the features derived from these representations, especially including quantification of change.

A device according to at least one embodiment of the invention for automatic determination of the change of a hollow organ comprises:
  a data interface designed for receiving a first medical image of the organ recorded at a first point of time, and a second medical image of the organ recorded at a second point of time,
  a segmentation unit designed for computing a first representation of the organ in the first image and a second representation of the organ in the second image, and
  a reference unit designed for computing a first reference-line of the organ based on the first representation of the organ and a second reference-line of the organ based on the second representation of the organ.

A medical imaging system, e.g. a magnetic resonance imaging system or a computer tomography system, comprises a control device according to at least one embodiment of the invention.

A method for automatic determination of a change of an organ, of at least one embodiment, comprises:
  providing a first medical image of the organ recorded at a first point of time;
  computing a first representation of the organ in the first medical image;
  computing a first reference-line of the organ based on the first representation of the organ computed;
  providing a second medical image of the organ recorded at a second point of time;
  computing a second representation of the organ in the second medical image;
  computing a second reference-line of the organ based on the second representation of the organ computed;
  registering of the first reference-line and the second reference-line of the organ to obtain at least one of matched representations of the organs and features derived from the first reference-line and the second reference-line of the organ; and
  comparing the at least one of the matched representations of the organ and the features derived from the matched representations organ.

A device, for automatic determination of a change of an organ, of at least one embodiment, comprises:
  a data interface to receive a first medical image of the organ recorded at a first point of time, and a second medical image of the organ recorded at a second point of time;
  a segmentation unit to compute a first representation of the organ in the first image received and a second representation of the organ in the second image received;
  a reference unit to compute a first reference-line of the organ based on the first representation of the organ and a second reference-line of the organ based on the second representation of the organ;
  a registration-unit to register the first reference-line computed and the second reference-line computed, to obtain at least one of matched representations of the organ and features derived from the matched representations of the organ computed; and a comparison-unit to compare at least one of the matched representations of the organ and the features derived from the matched representations of the organ computed.

At least one embodiment is directed to a non-transitory computer program product storing a computer program, directly loadable into a device or a control device for a medical imaging system, including program elements for performing the method of an embodiment when the computer program is executed by the device or the control device.

At least one embodiment is directed to a non-transitory computer-readable medium, storing program elements, readable and executable by a computer unit to perform the method of an embodiment when the program elements are executed by the computer unit.

BRIEF DESCRIPTION OF THE DRAWINGS

Other objects and features of the present invention will become apparent from the following detailed descriptions of example embodiments considered in conjunction with the accompanying drawings. It is to be understood, however, that the drawings are designed solely for the purposes of illustration and not as a definition of the limits of the invention.

In the diagrams, like numbers refer to like objects. Objects in the diagrams are not necessarily drawn to scale.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising,"

"includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method according to at least one embodiment of the invention for automatic determination of the change of a hollow organ, typically on the basis of medical images, and especially also for the visualization of the results, comprises:

providing a first medical image of the organ, e.g. the aorta, recorded at a first point of time, computing a first representation of the organ, e.g. a segmentation mask, in the first image, computing a first reference-line of the organ (i.e. a series of points in 3D space characterized by their spatial coordinates, e.g. a centerline) based on the first representation of the organ, providing a second medical image of the organ recorded at a second point of time, computing a second representation of the organ in the second image, computing a second reference-line of the organ based on the second representation of the organ, registering of the first and the second reference line to obtain a matching of the two representations of the organ and/or features derived from the representations, comparing the matched representations of the organ and/or the features derived from these representations, especially including quantification of change.

In addition, the results can be displayed for a user, as described in more detail below.

Concerning the expression "features" (can also be denominated as "properties" or "measurements" or "datasets"), the features represent a set of parameter values determined in the images. These parameters can be e.g. distances, cross sections or other "features" of the organ that can be measured. It is preferred that a feature comprises a whole set of parameter values measured along a predefined part of the reference-line (e.g. the whole reference-line).

Regarding the steps providing the medical images of the hollow organ, they should be recorded at two different points of time, one earlier (e.g. the first point of time) and one later (e.g. the second point of time). The organ may have changed between the two points of time and that change will be visible with this method. Although it is preferred that the images are 3D images, they also could be 2D images or stacks of 2D images. It is not important, what recording technique is used. However, the images should be digital images (or digitalized images) and are preferably CT-images (CT: computer tomography), MR-images (MR: magnet resonance), X-ray images or ultrasound images, e.g. from thoracic and/or abdominal (CT/MRI) acquisitions. Surely, the images should be from the same organ of the same patient. However, it is also possible, that the images are from two different patients in order to compare the two (similar) organs. These images are in the further process used to determine (and visualize) the change (progression or shrinkage) of the hollow organ under investigation.

Regarding the representations of the organ in the images it should be noted that initially there are only pixels (here, "pixel" also stands for "voxel") in the images. The organ must be made "known" for the method for that only the organ in the images is treated. Thus, the method determines the representation of the organ, that is the pixels representing the organ in the images, or another computerized representation as e.g. a surface mesh created from the pixels, an implicit formulation or a segmentation mask. For the following steps, this representation of the organ under investigation from the two images is used. For example, for the aorta these masks might have been obtained automatically using an automatic detection and quantification of the organ from the medical images, i.e. by performing automatic segmentation of the organ. However, the representation could also be generated manually or semi-automatically.

Regarding the steps of computing the reference-lines of the organ, the representations of the organ are used, since they represent the organ and not the information of the whole images. A reference line is a (typically theoretical) line characterizing the shape of the organ (e.g. straight or curved). Preferably, the reference line follows the outer/inner shape and/or the course of the hollow organ in the body of a patient. For two identical organs the reference lines are also identical.

A preferred reference line is the centerline, i.e. a line leading through the center points of the cross sections of the hollow organ. A preferred calculation of a centerline is based on an iterative calculation of a point d of the centerline based on a known point $d_{prev}$ (previously calculated) on the centerline, wherein point d has a definite distance δ to point $d_{prev}$ (or in a mathematical notation: $\|d-d_{prev}\|=δ$). For calculating the centerline, the optimization problem $$\min_d \max_{p \in S} \|d-p\| \qquad (1)$$

has to be solved, wherein S is the set of all points on the surface of the hollow organ and p is a point in S. To achieve a smooth centerline, it is preferred to include a regularization that confines the changes in the direction of the centerline. As an initial starting point, an anatomically unique defined point should be chosen, e.g. a point in the center of a cross section of the organ, preferably at one end on the picture of the organ. The center line follows the length of the organ, e.g. the vector of a laminar blood flow in a blood vessel.

However, other lines are also preferred as reference lines, e.g. a line following the surface or the wall of the organ (or a number of lines representing the inner or outer shape of the organ, where in the lines of a mesh could also be used as reference lines). The line does not necessarily need to follow the shape of the organ directly but may follow the shape e.g. in a spiral way. The reference line does not have necessarily to be one single line but can e.g. comprise two or more lines or may split or branch (e.g. when characterizing the bronchia or blood vessels, such as the pulmonary artery or the carotid artery).

Regarding the registration of the first and the second reference line, the goal is to determine a mapping of each point on one of the reference lines to a unique point on the other reference line. Using this mapping, the organ representations and/or features derived from the representations can be compared to each other. Typically, one reference line serves as target and the other reference line is transformed to match this target (wherein however, it is also possible to transform both sides). The techniques of graphical registration (also known as co-registration) are well known. Since the reference lines may also characterize the inner or outer shape of the representation of the organ, or a mesh of this representation, the registering process can theoretically also be based on the shape of the complete representation of the organ, e.g. a surface mesh or a segmentation mask. The registration is preferably a rigid registration, wherein non-rigid registrations are also possible.

Regarding the comparison of the matched representations of the organ and/or between features derived from these representations, there are numerous possibilities. Distances, cross sections or volumes could be calculated in the representations of the organ and compared with another. Surely, they must be depending on characterizing coordinates that are similar in the two representations. Thanks to the registration, for each feature at a particular location of the organ in the first data set a matching feature at the corresponding location in the second data set exists and can be compared. Change can be quantified and visually highlighted. It should be noted that by comparing features derived from the representations, quantitative results can be achieved, absolute or differences or ratios. It should also be noted that differences between pixels in the images could also be a useful comparison, wherein the positions of these pixels would be the corresponding feature. Typically, the images are recorded with a similar medical imaging system and the features measured there are automatically comparable. However, if there is the need (e.g. if the organ is pictured bigger on one image), the images or at least the representations can also be registered, especially by using the same transformations used for registering the reference lines.

A device according to at least one embodiment of the invention for automatic determination of the change of a hollow organ comprises:
 a data interface designed for receiving a first medical image of the organ recorded at a first point of time, and a second medical image of the organ recorded at a second point of time,
 a segmentation unit designed for computing a first representation of the organ in the first image and a second representation of the organ in the second image, and
 a reference unit designed for computing a first reference-line of the organ based on the first representation of the organ and a second reference-line of the organ based on the second representation of the organ.

It should be noted that the device may comprise one single component of the respective units to compute both, first and second means, or an individual unit for the first means and an individual unit for the second means. For example, the reference unit may comprise two components, one to compute the first reference-line and one to compute the second reference-line, and one single segmentation unit for computing both, the first representation of the organ in the first image and the second representation of the organ in the second image.

The device, in an embodiment, further comprises:
a registration-unit designed for registering of the first and the second reference line to obtain a matching of the two representations of the organ and/or features derived from the representations,
a comparison-unit designed for comparing the matched representations of the organ and/or the features derived from these representations, especially including quantification of change.

A control device according to at least one embodiment of the invention for controlling a medical imaging system, e.g. a CT-system or an MRI-system, comprises a device according to the invention. Alternatively or additionally it is designed to perform the method according to the invention. The control device may comprise additional units or devices for controlling components of a medical imaging device, e.g. a CT-system or a MRI-system, such as a X-ray unit, a sequence control unit for measurement sequence control, a memory, a radio-frequency transmission device that generates, amplifies and transmits RF pulses, a gradient system interface, a radio-frequency reception device to acquire magnetic resonance signals and/or a reconstruction unit to reconstruct magnetic resonance image data.

A medical imaging system, e.g. a magnetic resonance imaging system or a computer tomography system, comprises a control device according to at least one embodiment of the invention.

Some units or modules of the device or the control device mentioned above can be completely or partially realized as software modules running on a processor of a device or a control device. A realization largely in the form of software modules can have the advantage that applications already installed on an existing system can be updated, with relatively little effort, to install and run these units of the present application.

At least one embodiment of the invention is also achieved by a computer program product with a computer program that is directly loadable into the memory of a device of a device or a control device of a medical imaging system, and which comprises program units to perform the steps of at least one embodiment of the inventive method when the program is executed by the control device or the device. In addition to the computer program, such a computer program product can also comprise further parts such as documentation and/or additional components, also hardware components such as a hardware key (dongle etc.) to facilitate access to the software.

At least one embodiment of the invention is directed to a computer readable medium such as a memory stick, a hard-disk or other transportable or permanently-installed carrier can serve to transport and/or to store the executable parts of the computer program product so that these can be read from a processor unit of a control device or a device. A processor unit can comprise one or more microprocessors or their equivalents.

Particularly advantageous embodiments and features of the invention are given by the claims, as revealed in the following description. Features of different claim categories may be combined as appropriate to give further embodiments not described herein.

A preferred method of at least one embodiment comprises:
determining a first set of distances and/or cross sections from a set of predefined coordinates of the first reference-line to a surface of the organ pictured in the first medical image, and
determining a second set of distances and/or cross sections from the set of predefined coordinates of the second reference-line to the surface of the organ pictured in the second medical image.

These distances and/or cross sections are features derived from the representations mentioned above. The surface of the organ thereby denotes the set of points belonging to the surface of the representation of the organ, e.g. the vertices of the surface mesh or the pixels at the boundary of the segmentation mask. The distances and cross sections are measured from predefined coordinates of the reference lines to points on the surface of the organ. Due to the prior registration of the reference lines the coordinates and hence the points on the first and the second representation pairwise correspond. Thus, the measured distances and cross sections are pairwise comparable.

Regarding an embodiment, the method can include determining changes between the distances and/or cross sections, which can be achieved in at least one embodiment by comparing the first set of distances and/or cross sections with the second set of distances and/or cross sections of corresponding coordinates of the reference lines. This is achieved by comparing the measured distances and/or cross sections pairwise with the respective matched distance and/or cross section. It should be noted that a distance or cross section in the first representation should be compared with the corresponding distance or cross section (of a pair of distances or cross sections) in the second representation (i.e. for each distance/cross section in one image there should be a corresponding distance/cross section in the other image). It is preferred that this is done by computing ratios and/or differences of corresponding distances and/or cross sections. For example, this comparison is performed by computing ratios characterizing a relative change, e.g. the change of a cross-sectional area in %, or differences characterizing an absolute change, e.g. the change of the maximum diameter in mm.

Regarding at least one embodiment of the device, it is preferred that it additionally comprises:
a measurement unit designed for determining a first set of distances of a set of predefined coordinates of the first reference-line to a surface of the organ pictured in the first medical image and/or determining a set of cross-sections of the organ at a predefined coordinate of the first reference line pictured in the first medical image and determining a second set of distances of the set of predefined coordinates of the second reference-line to the surface of the organ pictured in the second medical image and/or determining a set of cross-sections of the organ at the predefined coordinate of the second reference line pictured in the second medical image,
wherein the registration unit is designed for registering the two reference lines to obtain a matching representation of the organ, and the comparison-unit is designed for comparing the measured distances and/or cross sections pairwise with the respective matched distances and/or cross sections, especially including a quantification of change. Thus, the comparing unit is designed for determining changes between the distances by comparing the first set of distances and/or cross sections with the second set of distances and/or cross sections of corresponding coordinates of the reference lines, preferably by computing ratios and/or differences of corresponding distances and/or cross sections. The measuring unit is preferably be part of the comparison-unit.

According to a preferred method of at least one embodiment, the reference-lines are centerlines of the hollow organ. These centerlines are preferably determined by an iterative calculation. In the course of this calculation, the next point d of a centerline is computed based on a known or pre-defined point $d_{prev}$ on the centerline with a predefined distance (δ, see above) between points d and $d_{prev}$ and the surface S of the hollow organ by solving the optimization problem $\min_d \max_{p \in S} \|d-p\|$ (see above formula (1)).

According to a preferred method of at least one embodiment, measurements are performed for the organ in order to obtain (relative and/or absolute) values of the size of parts of the organ. Preferably, the measurements are performed for a predefined set of points of the reference line, especially each (digital) point on the reference-line. The measurements preferably include the maximum diameter of the organ and/or the average diameter of the organ and/or the cross-sectional area of the organ at a predefined coordinate on the reference-line. For example, as a result, 1D profiles of the measurements along each centerline can be generated characterizing e.g. the course of the maximum diameter along the aorta. After that, the measurements from the two datasets can be compared point-by-point for predefined points on the centerline.

According to a preferred method of at least one embodiment, the reference lines are registered by using numerical optimization techniques. It is preferred that the registration is performed by applying a rigid or non-rigid spatial transformation, especially a transformation of the shift, rotation, stretch and/or warp, to the points on one of the centerlines. Typically, the registration is performed in order to get the best match between the two centerlines, i.e. to obtain a set of pairwise matching points on the two centerlines.

According to a preferred method of at least one embodiment, the matching points on the two reference lines are used for determining changes between the features derived from the representations of the organ. It should be noted that each matching point corresponds to a matching point on the first reference line (to form a pair as mentioned above).

According to a preferred method of at least one embodiment, the determined changes between the representations of the organ and/or between features determined from these representations are visualized. This is preferably done in form of a 3D-image showing the representation of the organ and the determined changes. Alternatively or additionally, this is preferably done in form if a 2D-diagram, wherein the points along the reference line are interpreted as points on one axis of the 2D diagram and the changes relative to each point is shown on the other axis. Especially, the points along the reference line (e.g. a centerline) are interpreted as points along a (curved) first axis for a 2D-visualization. Then, die distances are mapped on a second axis corresponding to coordinates on the first axis. If the centerline has been sampled equidistantly, also those points on the axis should be equidistant. The measurements or their change are mapped to the other axis.

According to a preferred method of at least one embodiment, the determined changes between the representations of the organ and/or between features derived from these representations are labeled or marked depending on the quantity of change (including absolute quantities and/or relative quantities, e.g. ratios). In the case the quantity of change is bigger than a predefined threshold it is preferred that a warning is provided, especially in the form of a special label, a special marker, a warning message and/or an acoustic signal. According to a preferred visualization method, the surface of the organ of at least one of the two representations is rendered in 3D. In this case, the change of a particular measurement could be displayed as different colors across the surface of the organ. For each point on the surface the color is thereby chosen according to the value of the changes of the corresponding point relative to the reference line. Colors should be chosen to highlight significant change, e.g. mark a severe diameter increase in red and stable regions in green or a neutral color. Vice versa, in a post-operative scenario a successful shrinkage might be marked in green or blue.

According to a preferred method of at least one embodiment, a graphical filter function, preferably smoothing and/or a gaussian filter is applied to the features derived from the organ representations and/or to the image visualizing changes. The filter is e.g. applied before plotting to suppress noise in the visualization.

In a preferred device according to of at least one embodiment of the invention, components of the device are part of a data-network, wherein preferably the data-network and a medical imaging system (i.e. a magnetic resonance imaging system or a computer tomography imaging system which provide image data) are in data-communication with each other, wherein the data-network preferably comprises parts of the internet and/or a cloud-based computing system, wherein preferably the device according to the invention or a number of components of this system is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved via data interfaces and/or data transmission protocols.

In the context of "cloud computing", in a preferred embodiment of the method according to at least one embodiment of the invention, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system according to the invention, the abovementioned units (data interface, the mentioned units) are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

The proposed measurement and visualization system allows for a fully automatic quantitative comparison of the size parameters (diameter, cross-sectional area) of hollow organs, in particular vessels depicted in two imaging data sets (in particular if combined with an automatic detection and segmentation technique). Moreover, the advanced visualization allows for a very intuitive and fast interpretation of the measured change.

Figure 1:
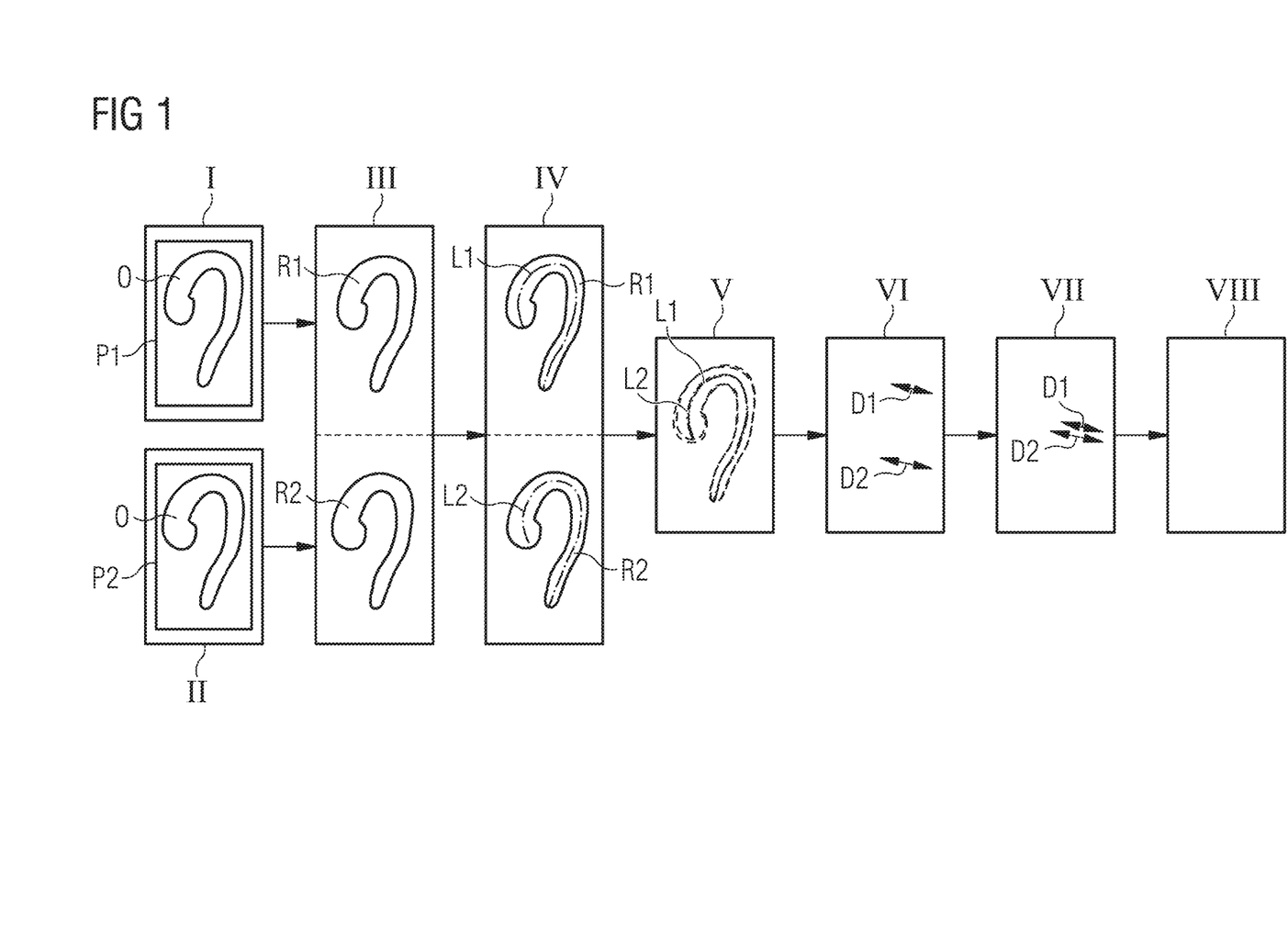
FIG. 1 shows a block diagram of the process flow of a preferred method according to an embodiment of the invention.
Figure 3:
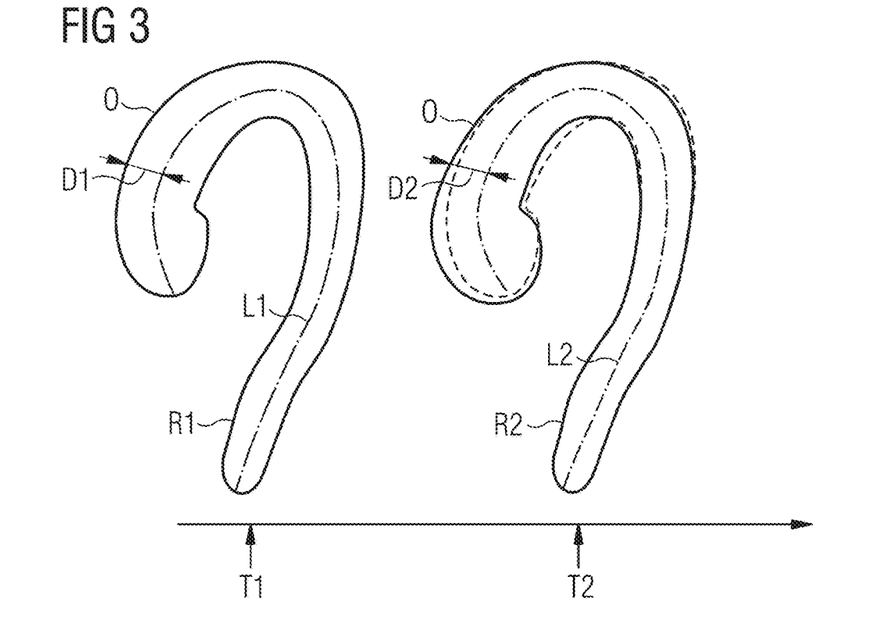
FIG. 3 shows two representations of an organ obtained from two CT data sets at two time points T0 and T1.

FIG. 1 shows a block diagram of the process flow of a preferred method according to an embodiment of the invention for automatic determination of the change of a hollow organ O (see. e.g. FIG. 3).

Figure 2:
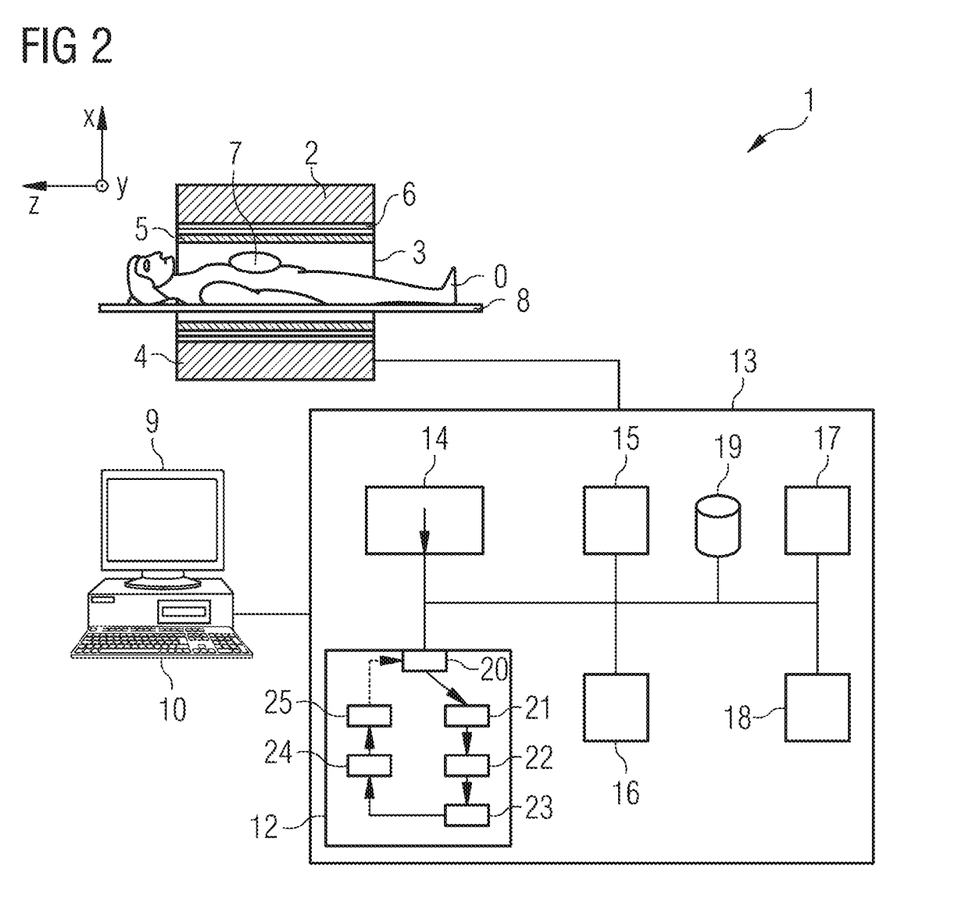
FIG. 2 shows a simplified MRI system as example for a medical imaging system with a device according to an embodiment of the invention.

In step I, a first medical image P1 of the organ O is provided that had been recorded at a first point of time, e.g. with an imaging device 1 as shown in FIG. 2.

In step II, a second medical image P2 of the organ O is provided that had been recorded at a (later) second point of time, e.g. also with an imaging device 1 as shown in FIG. 2.

In step III, a first representation R1 of the organ O in the first image P1 and a second representation R2 of the organ O in the second image P2 is computed. This could be performed in one single step or in two different (sub-)steps.

In step IV, a first reference-line L1 of the organ O is calculated based on the first representation R1 of the organ O, and a second reference-line L2 of the organ O is calculated based on the second representation R2 of the organ O. This could be performed in one single step or in two different (sub-)steps.

In step V, the reference-line L1 and L2 are registered obtaining matching representations of R1 and R2 of the organ O.

In step VI, a first set of features D1 (here e.g. distances D1 from a point of the reference line L1 to a point on the surface S of the organ O pictured in the first medical image P1) is determined at a set of predefined coordinates C1 of the first reference-line L1 and a second set of features D2 (here e.g. distances D2 from a point of the reference line L2 to a point on the surface S of the organ O pictured in the second medical image P2) is determined at the set of predefined coordinates C2 of the second reference-line L2. For this step, see also FIG. 3.

In step VII, changes between the features D1, D2 are determined by comparing the first set of features D1 with the second set of features D2 of corresponding coordinates C1, C2 of the reference lines L1, L2, preferably by computing ratios and/or differences.

In step VIII, the determined changes are visualized.

FIG. 2 shows a schematic representation of a magnetic resonance imaging system 1 ("MRI-system"). This example should show that not only CT-images could be used, but images recorded with any other medical imaging system. There could even be compared two images recorded with different medical imaging systems.

The MRI system 1 includes the actual magnetic resonance scanner (data acquisition unit) 2 with an examination space 3 or patient tunnel in which a patient or test person is positioned on a driven bed 8, in whose body the actual examination object, the organ O is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed that 3D images P1, P2 can be recorded. It here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the invention can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started via the input unit (possibly in combination with the display unit 9), and in particular suitable control protocols can be selected (and possibly modified) with suitable series of pulse sequence as explained above.

The control device 13 comprises a device 12 designed to perform the method according to the invention. This device 12 comprises the following components that may appear to be software modules.

A data interface 20 designed for receiving a first medical image P1 of the organ O recorded at a first point of time, and a second medical image P2 of the organ O recorded at a second point of time.

A segmentation unit 21 designed for computing a first representation R1 of the organ O in the first image P1 and a second representation R2 of the organ O in the second image P2.

A reference unit 22 designed for computing a first reference-line L1 of the organ O based on the first representation R1 of the organ O and a second reference-line L2 of the organ O based on the second representation R2 of the organ O.

A registration-unit 23 designed for registering of the first reference-line L1 and the second reference-line L2 to obtain a matching of the two representations R1, R2 of the organ O and/or features D1, D2 derived from the representations R1, R2.

A measuring unit 24 designed for determining a first set of distances D1 from a set of predefined coordinates C1 of the first reference-line L1 to a surface of the organ O pictured in the first medical image P1 (see e.g. the following figures) and a second set of distances D2 from the set of predefined coordinates C2 of the second reference-line L2 to the surface of the organ O pictured in the second medical image P2.

A comparison-unit 25 designed for comparing the matched representations R1, R2 of the organ O and/or the features D1, D2 derived from these representations R1, R2. The measuring unit 24 could also be a part of the comparison unit 25.

The results could be sent to the data interface 20 again, if it is a bilinear interface (dashed arrow) and shown on the display unit 9.

The MRI system 1 according to an embodiment of the invention, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

FIG. 3 shows two representations R1, R2 of an organ O in form of segmentation masks of two images P1, P2 of the aorta obtained from two CT data sets (images P1, P2, see e.g. FIG. 1) at two time points T1 and T2. The images P1, P2 could also be acquired by an MRI-system as shown in FIG. 1. These segmentation masks are obtained from two images P1, P2 that have been recorded a few months after another. It can be seen that the aortic root is larger in the right representation R2 as compared to the left representation R1 (dashed lines in the right representation R2 represent the shape of the left representation R1). In the representations R1, R2 centerlines L1, L2 are shown and a distance D1, D2 for each representation R1, R2. The distance should represent a feature, wherein typically, a feature is preferably a plurality of distances, especially distances measured to points on the wall of the organ throughout the whole reference line.

Figure 4:
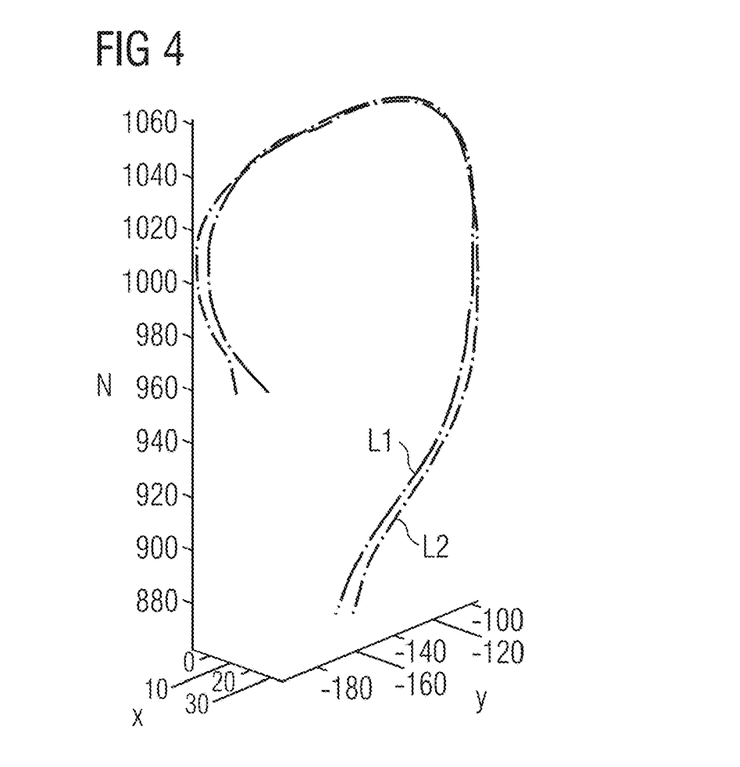
FIG. 4 shows registered centerlines obtained from the two representations displayed in FIG. 1.

FIG. 4 shows the aligned (co-registered) centerlines L1, L2 in a 3D space obtained from the two representations displayed in FIG. 2. The unit of the measures is mm.

Figure 5:
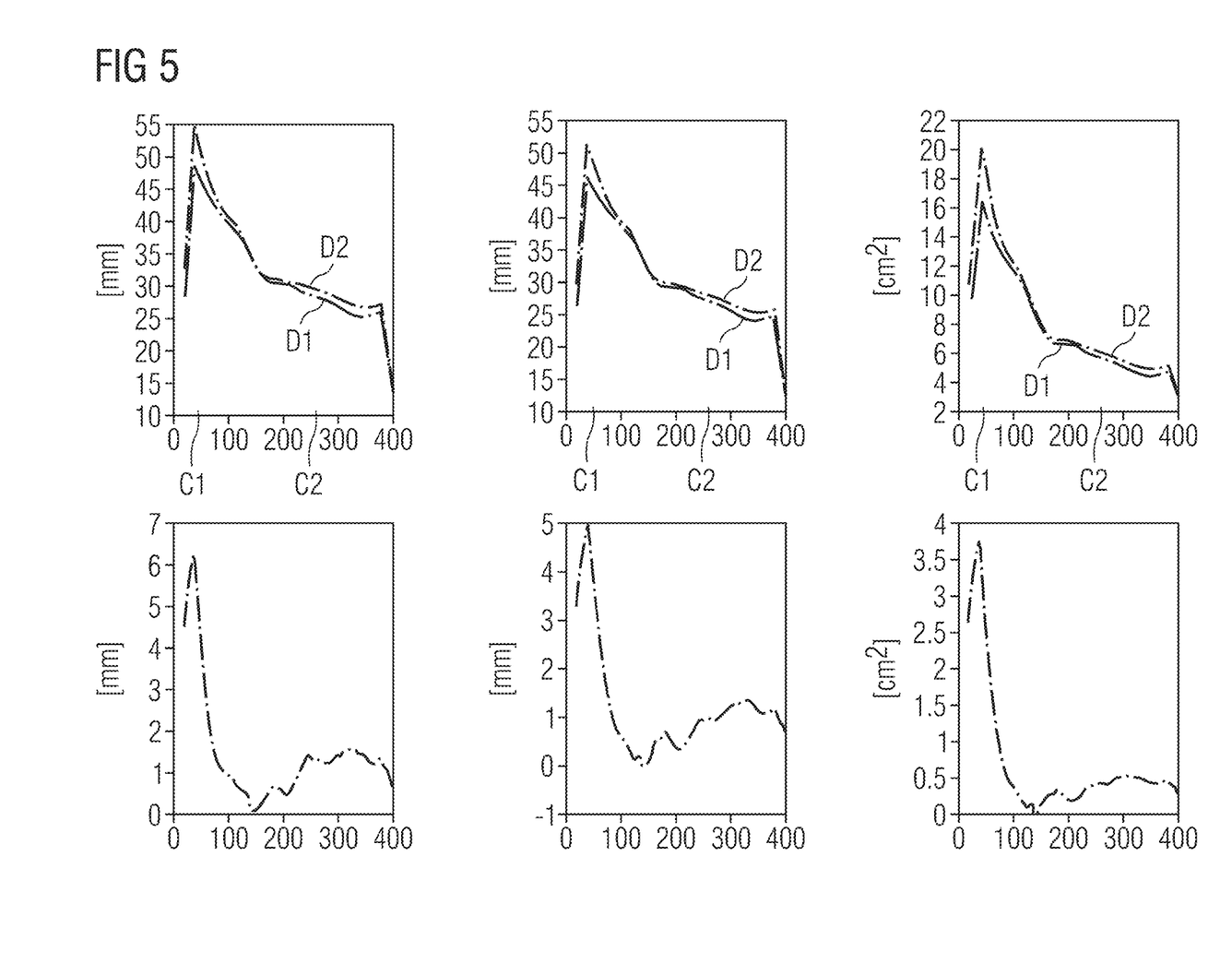
FIG. 5 shows the plots of three measurements as well as their difference.

FIG. 5 shows the plots of three features (measurements) (upper graphs) as well as their difference (lower graphs). The coordinates C1, C2 of the centerlines L1, l2 are mapped to the x-axis of the graphs and the differences of the features for the coordinates C1, C2 are shown on the y-axis. From left to right, the maximum diameter (left), the average diameter (middle) and the cross-sectional area (right) are plotted.

Figure 6:
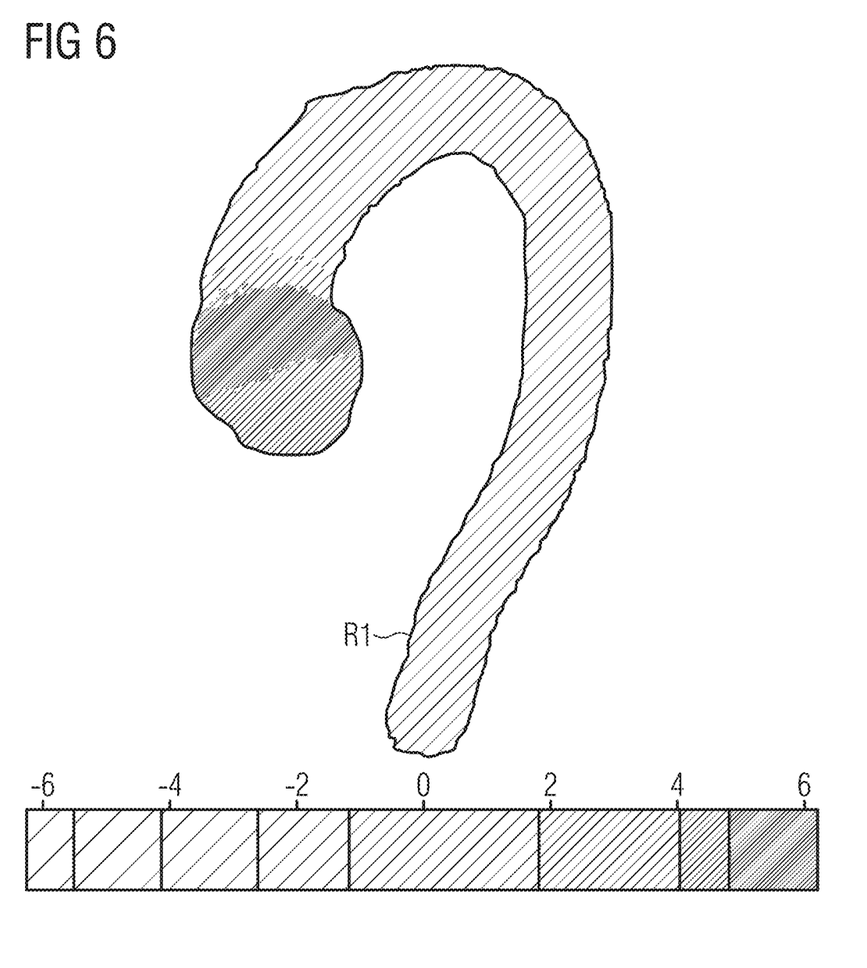
FIG. 6 shows a change in maximum diameter in 3D.

FIG. 6 shows the change in maximum diameter in 3D. Here the representation R1 of the first image P1 is shown with hatching structures. The greater the difference between distances D1, D2 is, the denser is the hatching.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic determination of a change of an organ, the method comprising:

computing a first representation of the organ in a first medical image, the first medical image being recorded at a first time;

computing a first centerline of the organ based on the first representation of the organ, the computing the first centerline including performing a first iterative calculation of a next point d of the first centerline based on a first known or defined point $d_{prev}$ on the first centerline;

computing a second representation of the organ in a second medical image, the second medical image being recorded at a second time;

computing a second centerline of the organ based on the second representation of the organ, the computing the second centerline including performing a second iterative calculation of a next point d of the second centerline based on a second known or defined point $d_{prev}$ on the second centerline;

registering the first centerline and the second centerline to obtain at least one of matched representations of the organ, or features derived from the matched representations; and comparing the at least one of the matched representations or the features.

2. The method of claim 1, further comprising:

determining at least one of first distances or first cross sections from a set of coordinates of the first centerline to a surface of the organ in the first medical image;

determining at least one of second distances or second cross sections from a set of coordinates of the second centerline to the surface of the organ in the second medical image;

obtaining a matching of the at least one of first distances or first cross sections and the at least one of second distances or second cross sections based on the registering; and pairwise comparing at least one of respective distances or respective cross sections among the at least one of first distances or first cross sections and the at least one of second distances or second cross sections based on the matching.

3. The method of claim 1, wherein each of the first iterative calculation and the second iterative calculation is performed with a defined distance between points d and $d_{prev}$ and points p on a surface S of the organ by solving an optimization problem $\min_d \max_{p \in S} \|d-p\|$.

4. The method of claim 1, further comprising:

performing measurements to obtain respective size values of parts of the organ.

5. The method of claim 4, wherein the performing measurements performs measurements for a defined set of points of the first centerline or the second centerline; and the measurements include at least one of a maximum diameter of the organ at a defined coordinate on the first centerline or the second centerline, an average diameter of the organ at the defined coordinate on the first centerline or the second centerline, or a cross-sectional area of the organ at the defined coordinate on the first centerline or the second centerline.

6. The method of claim 1, wherein the registering registers the first centerline and the second centerline using a numerical optimization techniques.

7. The method of claim 6, wherein the registering registers the first centerline and the second centerline by applying a rigid or non-rigid spatial transformation to points on one of first centerline or the second centerline.

8. The method of claim 1, further comprising:

determining changes between the at least one of the matched representations or the features including matching each respective point among a plurality of points on the second centerline to a corresponding point among a plurality of points on the first centerline.

9. The method of claim 8, wherein the determining determines changes between the features based on the matching.

10. The method of claim 1, further comprising:

visualizing changes between the at least one of the matched representations or the features based on the comparing.

11. The method of claim 10, further comprising:

applying a graphical filter function to at least one of the features or an image visualizing the changes.

12. The method of claim 1, further comprising:

labeling or marking changes between the at least one of the matched representations or the features based on the comparing, wherein the labeling or the marking depends on a respective quantity of each change among the changes.

13. The method of claim 1, wherein the computing the first representation of the organ includes segmenting the first representation from the first medical image; and the computing the first centerline computes the first centerline based on the first representation of the organ after the segmenting.

14. The method of claim 1, wherein the comparing includes determining a first distance or a first cross section corresponding to the first medical image, and determining a second distance or a second cross section corresponding to the second medical image; and the method further comprises determining a ratio based on (i) the first distance and the second distance or (ii) the first cross section and the second cross section.

15. The method of claim 1, wherein the comparing includes determining a quantity of the change of the organ; and the method further includes outputting a label, a marker, a warning message or an acoustic signal in response to determining the quantity of the change exceeds a threshold.

16. A device for automatic determination of a change of an organ, the device comprising:

a segmentation unit to compute a first representation of the organ in a first medical image and a second representation of the organ in a second medical image, the first medical image being recorded at a first time, and the second medical image being recorded at a second time;

a reference unit to compute a first centerline of the organ based on the first representation of the organ and to compute a second centerline of the organ based on the second representation of the organ, computation of the first centerline including performing a first iterative calculation of a next point d of the first centerline based on a first known or defined point $d_{prev}$ on the first centerline, and computation of the second centerline including performing a second iterative calculation of a next point d of the second centerline based on a second known or defined point $d_{prev}$ on the second centerline;

a registration unit to register the first centerline and the second centerline to obtain at least one of
matched representations of the organ, or
features derived from the matched representations; and
a comparison unit to compare the at least one of the matched representations or the features.

17. The device according to claim 16, further comprising;
a measuring unit configured to determine
at least one of first distances or first cross sections from a set of defined coordinates of the first centerline to a surface of the organ in the first medical image, and
at least one of second distances or second cross sections from a set of defined coordinates of the second centerline to the surface of the organ in the second medical image, wherein
the registration unit is configured to obtain a matching of the at least one of first distances or first cross sections and the at least one of second distances or second cross sections based on the registration of the first centerline and the second centerline, and
the comparison unit is configured to pairwise compare at least one of respective distances or respective cross sections among the at least one of first distances or first cross sections and the at least one of second distances or second cross sections based on the matching.

18. A control device for controlling a medical imaging system, comprising the device of claim 16.

19. A medical imaging system comprising the control device of claim 18.

20. A non-transitory computer-readable medium, storing program elements that, when executed by a computer unit, cause the computer unit to perform a method for automatic determination of a change of an organ, the method comprising:
computing a first representation of the organ in a first medical image, the first medical image being recorded at a first time;
computing a first centerline of the organ based on the first representation of the organ, the computing the first centerline including performing a first iterative calculation of a next point d of the first centerline based on a first known or defined point $d_{prev}$ on the first centerline;
computing a second representation of the organ in a second medical image, the second medical image being recorded at a second time;
computing a second centerline of the organ based on the second representation of the organ, the computing the second centerline including performing a second iterative calculation of a next point d of the second centerline based on a second known or defined point $d_{prev}$ on the second centerline;
registering the first centerline and the second centerline to obtain at least one of matched representations of the organ, or
features derived from the matched representations of the organs; and
comparing the at least one of the matched representations or the features.

* * * * *